Jan. 29, 1974 P. W. HOLMQUIST ET AL Plant Pat. 3,459
CHRYSANTHEMUM PLANT
Filed June 5, 1972
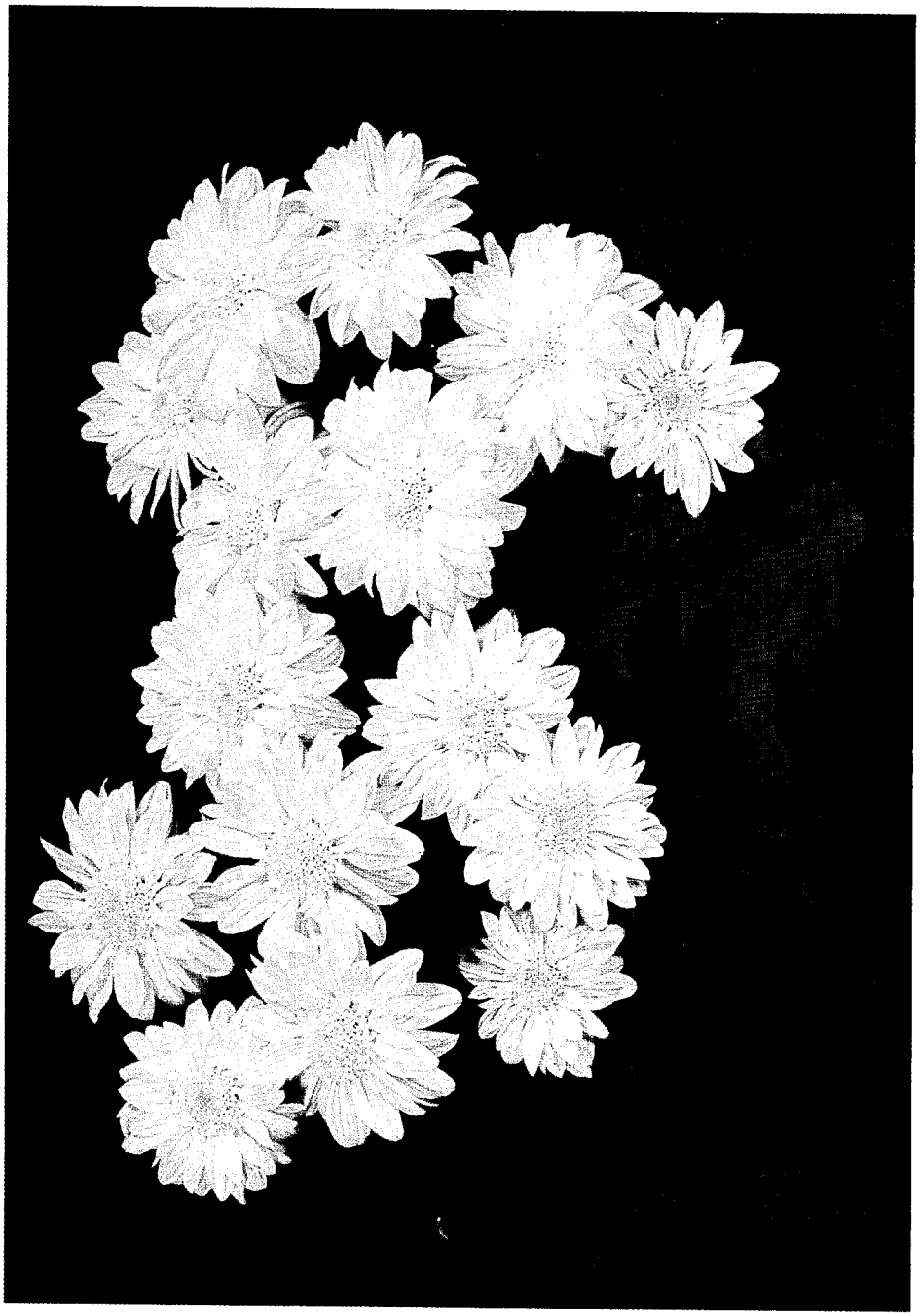

United States Patent Office

Plant Pat. 3,459

Patented Jan. 29, 1974

3,459
CHRYSANTHEMUM PLANT

Philip W. Holmquist, 4045 Highway 101, Hamel, Minn. 55340, and Walter H. Jessel, Jr., Doylestown, and William E. Duffett, Akron, Ohio; said Jessel and said Duffett assignors to said Holmquist

Filed June 5, 1972, Ser. No. 259,996
Int. Cl. A01h *5/00*
U.S. Cl. Plt.—74 1 Claim

The present invention comprises a new and distinct cultivar of chrysanthemum plant which is a sport of the unpatented cultivar known commercially in the United States as Nimbus.

The new cultivar is similar in many respects to Nimrod, likewise an unpatented but commercial cultivar and a sport of Nimbus, having the same characteristics as Nimrod of:

(1) Flower form and size.
(2) Plant habit.
(3) Foliage shape.

Ohio, the new cultivar has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color and total vigor may vary significantly with varying environmental conditions such as temperature, day length, and light intensity. Suggested flowering in the northern and western United States is from April through October; coastal California, April through October; in the South, March through November. Flowering is not recommended for Florida.

The accompanying photographic drawing shows the unique color characteristic of the new cultivar, with the new cultivar appearing on the left and the cultivar Nimrod on the right.

In the following description, color references are made both to the Royal Horticultural Color Society Chart (R.H.S.) and to the Munsell Color Book, 1963 edition. Color comparisons are made with the cultivar Nimrod.

Botanical classification: *Chrysanthemum morifolium*

| | Yellow Nimrod | Nimrod |
|---|---|---|
| Bloom: | | |
| Size | 3″–3¼″ | |
| Fully expanded | 3¾″–4″ | |
| Borne | Clusters on elongate pedicels | |
| Stems | Strong and wiry | |
| Form | Tightly crested anemone | |
| Permanence | 7–10 days | |
| Color (Munsell): | | |
| Center of flower | Yellow green 2.5GY8/10 to yellow 5Y7/10 | Yellow green 2.5GY8/10 to yellow 5Y7/10. |
| Base of petals | Yellow green 2.5GY8/10 | Yellow green 2.5GY8/10. |
| Inside of petals | Yellow 7.5Y8.5/10 to light yellow 10Y9/4 | White N9.5/. |
| Reverse of petals | Yellow 10Y9/6 to light yellow 10Y9/4 | Do. |
| Tonality from a distance | Yellow | White. |
| Discoloration | Light yellow 10Y9/4 | White N9.5/. |
| Color (R.H.S.): | | |
| Center of flower | Yellow-green group 144C, yellow group 11A | Yellow-green group 144C, yellow group 11A. |
| Base of petals | Yellow-green group 144C | Yellow-green group 144C. |
| Inside of petals | Yellow group 3A to yellow group 3D | White group 155D. |
| Reverse of petals | Yellow group 3C to yellow group 3D | Do. |
| Petals: | | |
| Texture | Smooth | |
| Appearance and form | Closed at base, opening quickly to a multi-ridged flat keel, tapering to a blunt tip. | |
| Arrangement | Composite, whorled on a single receptacle | |
| Persistence | Resists shatter | |
| Fragrance | Typical chrysanthemum | |
| Reproductive organs: | | |
| Stamen, anthers | 200 or more | |
| Pollen | Abundant to none (functional sterility) | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 39″–43″ given 2–3 long day weeks and 11 to 12 weeks total crop time, as defined in the timetables of Yoder Brothers, Inc., Barberton, Ohio, for the various seasons of the year. | |
| Spread | None grown single stem to slight when pinched | |
| Foliage: | | |
| Top side | Very dark green, 7.5GY2/4 | |
| Size | 5¾″ long, 3″ wide | |
| Quantity | Numerous | |
| Shape | Spatulate lobed | |
| Texture | Smooth | |
| Ribs and veins | Prominent | |
| Edge | Moderately indented | |
| Serration | Coarse | |
| Under side | Medium green, 7.5GY4/4 | |
| Stipules | Prominent | |

(4) Recommended period of flowering, and flowering response.

The new cultivar is distinguished from Nimrod and also from the parent cultivar Nimbus by its yellow flower color.

The new cultivar was found discovered at Hamel, Minn., as a sectorial sport of the parent cultivar, with four of the five flowers on the spray displaying a yellow color. When asexually reproduced by cuttings at Barberton,

We claim:

1. A new and distinct cultivar of chrysanthemum characterized particularly as to its uniqueness when compared to the parent cultivar Nimbus and to the cultivar Nimrod by its yellow flower color.

No references cited.

ROBERT B. BAGWELL, Primary Examiner

UNITED STATES PATENT OFFICE
CERTIFICATE OF CORRECTION

Patent No. PP-3459 Dated January 29, 1974

Inventor(s) PHILIP W. HOLMQUIST, WALTER H. JESSEL, JR. and WILLIAM E. DUFFETT

It is certified that error appears in the above-identified patent and that said Letters Patent are hereby corrected as shown below:

In the tabulated description below columns 1 and 2, under "Bloom:", opposite "Borne", change "elongate" to --elongated--.

In the tabulated description below columns 1 and 2, under "Plant:", opposite "Height" change "39" - 43" " to --39" - 42"--.

Signed and sealed this 1st day of October 1974.

(SEAL)
Attest:

McCOY M. GIBSON JR.
Attesting Officer

C. MARSHALL DANN
Commissioner of Patents